(12) United States Patent
Maebashi et al.

(10) Patent No.: US 10,504,688 B2
(45) Date of Patent: *Dec. 10, 2019

(54) ANALYTICAL CELL AND METHOD OF PRODUCING THE SAME

(71) Applicant: HONDA MOTOR CO., LTD., Minato-Ku, Tokyo (JP)

(72) Inventors: Takanori Maebashi, Wako (JP); Nariaki Kuriyama, Wako (JP); Yoshiya Fujiwara, Wako (JP)

(73) Assignee: Honda Motor Co., Ltd., Tokyo (JP)

(*) Notice: Subject to any disclaimer, the term of this patent is extended or adjusted under 35 U.S.C. 154(b) by 33 days.

This patent is subject to a terminal disclaimer.

(21) Appl. No.: 15/195,276

(22) Filed: Jun. 28, 2016

(65) Prior Publication Data

US 2017/0003243 A1  Jan. 5, 2017

(30) Foreign Application Priority Data

Jul. 1, 2015  (JP) .................................. 2015-132566

(51) Int. Cl.
*H01J 37/20* (2006.01)
*H01M 10/42* (2006.01)
*G01N 23/2204* (2018.01)

(52) U.S. Cl.
CPC .......... *H01J 37/20* (2013.01); *G01N 23/2204* (2013.01); *H01M 10/4285* (2013.01);
(Continued)

(58) Field of Classification Search
CPC .......... H01J 37/185; H01J 37/20; H01J 37/16; H01J 37/29; H01J 37/18; H01J 37/26;
(Continued)

(56) References Cited

U.S. PATENT DOCUMENTS

| 9,548,184 B2 | 1/2017 | Creemer et al. |
| 2008/0003142 A1* | 1/2008 | Link .................... B01F 3/0807 422/82.08 |

(Continued)

FOREIGN PATENT DOCUMENTS

| JP | 2008-512841 A | 4/2008 |
| JP | 2010-151826 A | 7/2010 |

(Continued)

OTHER PUBLICATIONS

M. Gu, et al., Demonstration of an Electrochemical Liquid Cell for Operando Transmission Electron Microscopy Observation of the Lithiation/Delithiation Behavior of Si Nanowire Battery Anodes, Nano Lett., 13 (12), pp. 6106-6112 (2013).*

(Continued)

*Primary Examiner* — Maris R Kessel
(74) *Attorney, Agent, or Firm* — Carrier Blackman & Associates, P.C.; Joseph P. Carrier; William D. Blackman

(57) ABSTRACT

An analytical cell includes a first substrate and a second substrate each having a through hole extending in a thickness direction thereof. The first substrate and the second substrate are partially overlapped with each other to form an overlapping portion. In the overlapping portion, a solid state joint is formed by solid state bonding of a first solid portion protruding from the first substrate and a second solid portion protruding from the second substrate, whereby the first substrate and the second substrate are spaced from each other by a predetermined distance, and joined together in a state where the first substrate and the second substrate are positioned to form an observation window. At the observation window, the through holes of the first substrate and the second substrate face each other, and an electron beam is transmitted through the observation window.

8 Claims, 11 Drawing Sheets

(52) U.S. Cl.
CPC ............... *H01J 2237/2003* (2013.01); *H01J 2237/2802* (2013.01)

(58) Field of Classification Search
CPC ....... H01J 2237/2002; H01J 2237/2003; H01J 2237/2007; Y02E 60/128; G01N 27/00; G01N 27/06; G01N 27/07; G01N 27/08; G01N 27/10; G01N 27/128; G01N 27/28; G01N 27/283; G01N 27/30; G01N 27/403; G01N 27/413; G01N 27/416
See application file for complete search history.

(56) References Cited

U.S. PATENT DOCUMENTS

| | | | | |
|---|---|---|---|---|
| 2008/0135778 | A1* | 6/2008 | Liu | H01J 37/20 250/440.11 |
| 2008/0179518 | A1* | 7/2008 | Creemer | H01J 37/20 250/311 |
| 2010/0159606 | A1 | 6/2010 | Nakaminami et al. | |
| 2010/0193398 | A1* | 8/2010 | Marsh | G02B 21/34 206/710 |
| 2010/0276277 | A1* | 11/2010 | Chey | G01N 27/416 204/242 |
| 2013/0264476 | A1 | 10/2013 | Damiano, Jr. et al. | |

FOREIGN PATENT DOCUMENTS

| | | |
|---|---|---|
| JP | 2013-535795 A | 9/2013 |
| JP | 2014-186877 A | 10/2014 |

OTHER PUBLICATIONS

Y. Temiz, et al., Lab-on-a-chip devices: How to close and plug the lab?, Microelectronic Engineering, vol. 132, pp. 156-175 (available online Oct. 28, 2014) (Year: 2014).*

Y. Luo, et al., Ultrasonic bonding for thermoplastic microfluidic devices without energy director, Microelectronic Engineering, vol. 87, pp. 2429-2436 (2010) (Year: 2010).*

Unocic et al., "In-Situ Electron Microscopy of Electrical Energy Storage Materials", [online], 2011, retrieved on Mar. 27, 2015 from the Internet <URL: http://energy.gov/sites/prod/files/2014/03/f11/es095_unocic_2011_o.pdf> indicated in the English specification on p. 1.

Office Action dated Nov. 6, 2018, issued over the corresponding Japanese Patent Application No. 2015-132566, and the English translation thereof.

* cited by examiner

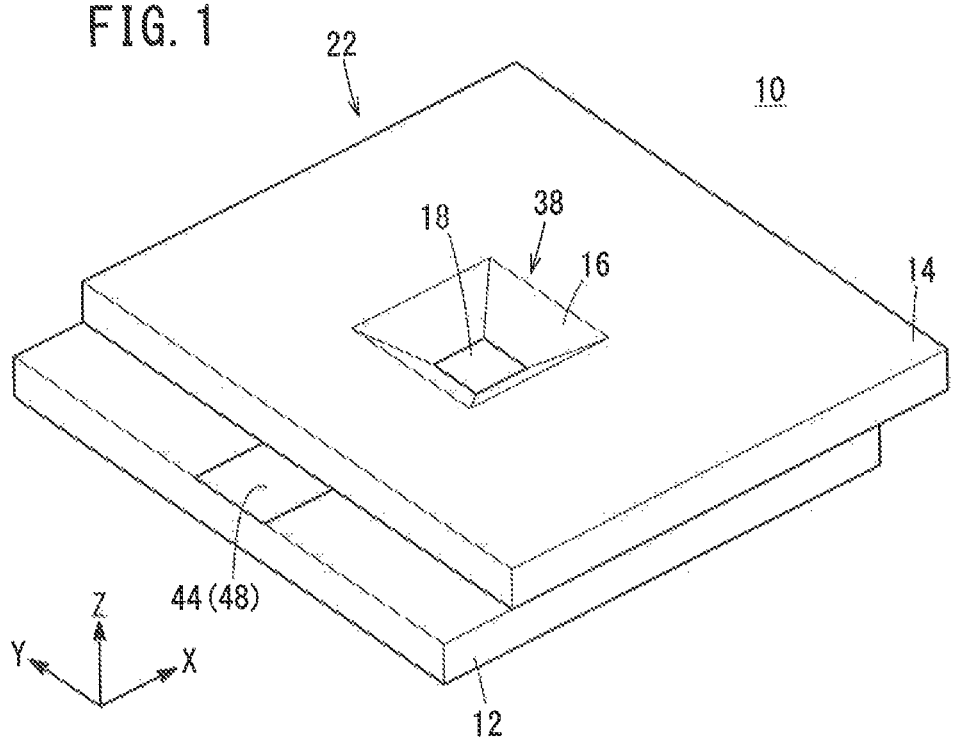

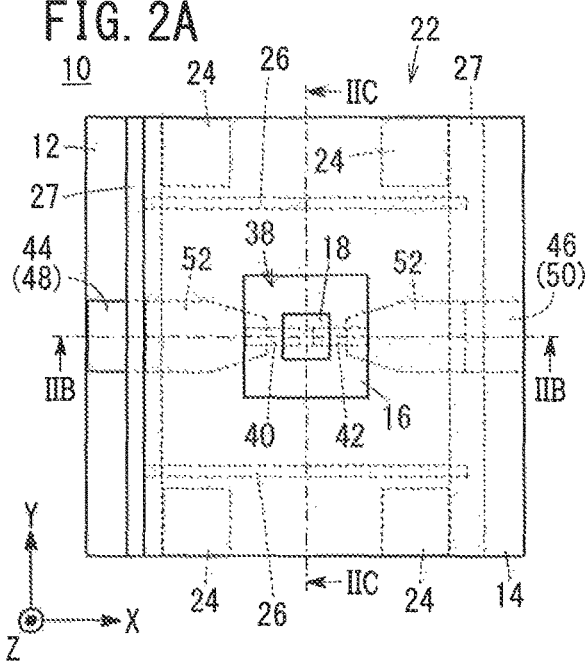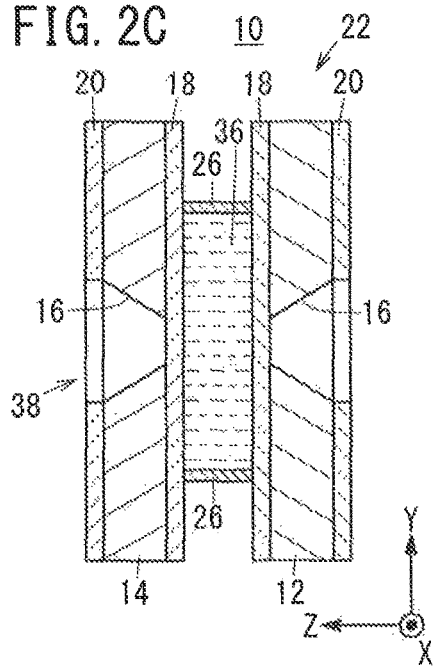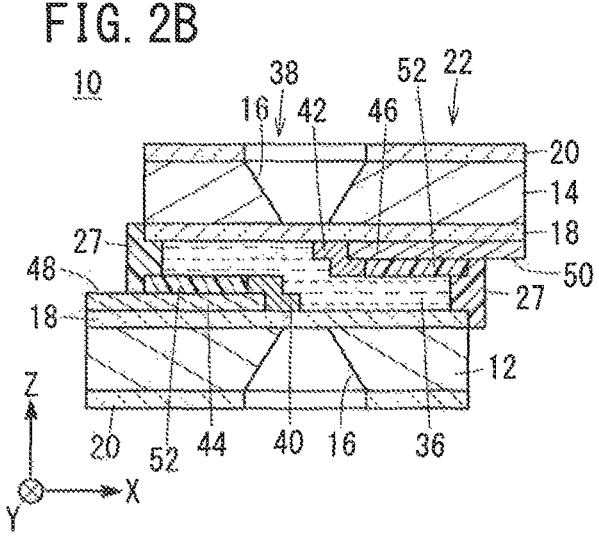

ANALYTICAL CELL AND METHOD OF PRODUCING THE SAME

CROSS-REFERENCE TO RELATED APPLICATION

This application is based upon and claims the benefit of priority from Japanese Patent Application No. 2015-132566 filed on Jul. 1, 2015, the contents of which are incorporated herein by reference.

BACKGROUND OF THE INVENTION

Field of the Invention

The present invention relates to an analytical cell suitable for use, e.g., in an electrode reaction analysis in analytical equipment, and a method of producing the analytical cell.

Description of the Related Art

As is well known, in an electric cell, a negative electrode active material and a positive electrode active material undergo electrode reactions in a charge-discharge process. In recent years, such electrode reactions have been analyzed during the charging/discharging process using analytical equipment. For example, an analytical cell that can be observed by a transmission electron microscope (TEM) has been proposed in In-situ Electron Microscopy of Electrical Energy Storage Materials [online], 2011, retrieved on Mar. 27, 2015 from the Internet <URL: http://energy.gov/sites/prod/files/2014/03/f11/es095_unocic_2011_o.pdf>.

This analytical cell contains a pair of substrates (silicon substrates). Each of the substrates has a rectangular observation window having a size of about 50 μm ×100 μm. The pair of substrates are partially overlapped with each other to form an overlapping portion. In the overlapping portion, the substrates are spaced from each other by a predetermined distance by a spacer interposed between the substrates. The substrates are positioned in a manner that the observation windows face each other. Further, a positive electrode active material containing $LiCoO_2$ and a negative electrode active material containing highly oriented graphite are deposited on one of the silicon substrates by an ion beam deposition method, such that the positive electrode active material and the negative electrode active material are located between the observation windows. It should be noted that each of the negative electrode active material and the positive electrode active material is extracted from a bulk body using a focused ion beam (FIB).

The negative electrode active material and the positive electrode active material (hereinafter also referred to as active materials, collectively) are electrically connected to a negative electrode collector and a positive electrode collector (hereinafter also referred to as collectors, collectively), respectively, inside the overlapping portion. Each of the collectors extends from the inside of the overlapping portion, such that one end side thereof is exposed to the outside. Therefore, the negative electrode active material and the positive electrode active material can be electrically connected to the charging/discharging devices, etc. outside the overlapping portion through the collectors, and it is possible to cause electrode reactions, etc.

In the case of analyzing electrode reactions, etc. of the analytical cell, for example, by a holder proposed in Japanese Laid-Open Patent Publication No. 2013-535795 (PCT), the analytical cell is held in the analytical equipment, and observed using a transmission electron microscope (TEM), etc. This holder includes a holder body having a pocket accommodating the analytical cell, and a holder lid attached to the holder body for fixing the analytical cell in the pocket.

For fixing the analytical cell to the holder, firstly, among a pair of substrates of the analytical cell, one substrate that does not have any active material is placed on the bottom wall in the pocket through an O-ring. Then, another substrate having active materials is overlapped with the one substrate through the spacer, and the analytical cell is assembled in the pocket. At this time, the side wall surface of the pocket is brought into abutment against the side surfaces of the substrates to thereby position the substrates in such a manner that observation windows are overlapped with each other.

Then, for sealing the opening of the pocket accommodating the analytical cell, O-rings are interposed between the substrate of the analytical cell and the holder lid, and the holder lid is attached to the holder body. In this manner, a pressure is applied from the holder body and the holder lid to the analytical cell through the O-rings provided at both ends in the overlapping direction. As a result, the analytical cell is fixed to the holder. Further, the substrates are prevented from being shifted from the state where the substrates are positioned with respect to each other in the manner as described above.

The holder has a flow channel for electrolytic solution inside the overlapping portion, and an electrical path for connecting each of the collectors to the charge-discharge tester or the like. Therefore, by allowing the electrolytic solution to flow through the analytical cell fixed to the holder as described above via the flow channel, and connecting the electrical path to the collectors, it is possible to cause electrode reactions by the active materials. The TEM observation is carried out while transmitting an electron beam through the observation window to analyze the electrode reactions of the active materials.

SUMMARY OF THE INVENTION

In the above analytical cell, the substrates are positioned with respect to each other by bringing the side surfaces of the substrates into abutment against the side wall surface of the pocket provided in the holder body. Therefore, in the case where the machining accuracy with respect to the pocket is not sufficient, it is difficult to position the substrates with respect to each other accurately.

Further, in the analytical cell assembled in the pocket, in a state where the holder lid is not attached to the holder body, the substrates are not fixed together. Therefore, there is a concern that positional displacement of the substrates may occur due to the pressure applied to the analytical cell through the O-rings, e.g., at the time of attaching the holder lid to the holder body.

Further, if the position where the pressure is applied to the substrates by contact with the O-rings does not coincide with the position of the spacer interposed between the substrates, moment is created on the substrates. In such a case, there is a concern that the distance between the substrates may deviate from a distance value which has been determined beforehand based on the thickness, etc. of the spacer.

In particular, since observation of the analytical cell by an electron microscope is performed under a high vacuum atmosphere, due to the influence of pressure change caused when evacuation is performed from the atmospheric pressure, the positional displacement between the substrates and changes in the distance between the substrates tend to become large.

Therefore, in the case of the above analytical cell, it is not possible to eliminate the concern that the accuracy of the analysis may be degraded because the observation windows are not formed with high accuracy due to the positional displacement of the substrates or the changes in the distance between the substrates.

A main object of the present invention is to provide an analytical cell having excellent analysis accuracy, by making it possible to position substrates with each other and set the distance therebetween easily and highly accurately, and to maintain the positioning and the distance.

Another object of the present invention is to provide a method of producing the above described analytical cell.

According to one aspect of the present invention, an analytical cell is provided. The analytical cell includes a first substrate and a second substrate which are partially overlapped with each other to form an overlapping portion. The overlapping portion is configured to allow electrolytic solution to be present between the first substrate and the second substrate. An observation window is formed in the overlapping portion for transmitting an electron beam through the observation window. Each of the first substrate and the second substrate has a through hole extending therethrough in a thickness direction thereof, and also has a transmission membrane having an electron beam permeability, the transmission membrane being disposed on one surface of each of the first substrate and the second substrate so as to cover one end of the through hole. In the overlapping portion, the first substrate and the second substrate are joined together by a solid state joint formed by solid state bonding of a first solid portion and a second solid portion, the first solid portion protruding from the first substrate, the second solid portion protruding from the second substrate. The first substrate and the second substrate are spaced from each other by a predetermined distance, and are positioned to form the observation window at a position where the through hole of the first substrate and the through hole of the second substrate face each other across the transmission membranes. In a space within the overlapping portion, a negative electrode active material and a positive electrode active material are provided, and the negative electrode active material and the positive electrode active material are spaced from each other, and contact the electrolytic solution individually. A negative electrode collector and a positive electrode collector extending from the inside of the overlapping portion to the outside thereof so as to be exposed to the outside, and the negative electrode collector and the positive electrode collector are electrically connected respectively to the negative electrode active material and the positive electrode active material inside the overlapping portion.

It should be noted that the term "solid state bonding (welding)" used in this specification means "General term for the method of welding performed at a temperature less than or equal to the melting point of a base material. In the method, welding of solid state materials are performed in a pressurized state or a non-pressurized state without using a brazing material." defined in JISZ3001-2"Welding Vocabulary Part 2: Welding Processes 4.2.7. Solid State Bonding No. 22701".

In the overlapping portion of the analytical cell according to the present invention, as described above, owing to the solid state joint, the first substrate and the second substrate are joined together in the state where the first substrate and the second substrate are spaced from each other by a predetermined distance, and positioned to form an observation window.

The distance between the first substrate and the second substrate (hereinafter referred to as "substrates" collectively) is substantially the same as the length of the solid state joint in the overlapping direction, and the length of the solid state joint in the overlapping direction is substantially the same as the sum of the protrusion lengths of the first solid portion and the second solid portion. Therefore, by adjusting the protrusion lengths of the first solid portion and the second solid portion, it is possible to set the distance between the substrates to a desired value easily.

Further, it is possible to position the substrates with respect to each other easily and highly accurately without accommodating the analytical cell in the pocket, etc. of the holder for holding the analytical cell in the analytical equipment, i.e., regardless of the machining precision, etc. of the holder. Further, the substrates are joined together by forming the solid state joint in the state where the substrates are positioned with respect to each other. Thus, at the time of attaching the analytical cell to the holder, and performing observation using the electron microscope in a high vacuum atmosphere, it is possible to suppress positional displacement between the substrates and occurrence of changes in the distance between the substrates effectively, and maintain the state where the substrates are positioned with a high degree of accuracy.

That is, in the analytical cell according to the present invention, since the observation window can be formed with a high degree of accuracy, and such a high degree of accuracy can be maintained, it is possible to analyze the electrode reactions, etc. of active materials accurately through the observation window.

In the analytical cell, preferably, the solid state joint is provided to seal at least one side of the overlapping portion. In this case, by the step of forming the solid state joint by solid state bonding of the first solid portion and the second solid portion, it is possible to form the overlapping portion by joining the substrates together, and seal sides of the overlapping portion to form a liquid-tight space, which is filled with the electrolytic solution, inside the overlapping portion. Therefore, production steps are simplified, and it becomes possible to obtain the analytical cell efficiently.

Further, according to another aspect of the present invention, a method of producing an analytical cell is provided. The analytical cell includes a first substrate and a second substrate which are partially overlapped with each other to form an overlapping portion. The overlapping portion is configured to allow electrolytic solution to be present between the first substrate and the second substrate. An observation window is formed in the overlapping portion at a position where a through hole of the first substrate and a through hole of the second substrate face each other, for transmitting an electron beam through the observation window. The method includes the steps of forming a first solid portion protruding from the first substrate and forming a second solid portion protruding from the second substrate, wherein the first solid portion and the second solid portion are formed respectively on portions of the first substrate and the second substrate that are face-to-face with each other when the first substrate and the second substrate are positioned to form the overlapping portion, positioning the first substrate and the second substrate to bring the first solid portion and the second solid portion into abutment against each other, and forming a solid state joint by solid state bonding of the first solid portion and the second solid portion that are in abutment against each other, for thereby allowing the first substrate and the second substrate to be spaced from each other by a predetermined distance, and thereby joining the first substrate and the second substrate together in a state where the first substrate and the second substrate are positioned.

In the present invention, it is possible to mutually position the substrates and set the distance between the substrates easily with a high degree of accuracy. Further, it is possible to maintain the positions of the substrates and the distance between the substrates. Therefore, it becomes possible to efficiently obtain an analytical cell having excellent analysis accuracy.

In the above method of producing the analytical cell, preferably, the solid state joint is formed to seal at least one side of the overlapping portion. In this case, the production steps can be simplified, and thus, it becomes possible to obtain the analytical cell even more efficiently.

The above and other objects, features and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 1 is an overall schematic perspective view of an analytical cell according to an embodiment of the present invention;

FIG. 2A is a plan view of the analytical cell in FIG. 1;

FIG. 2B is a cross sectional view of the analytical cell, taken along a line IIB-IIB indicated by arrows in FIG. 2A;

FIG. 2C is a cross sectional view taken along a line IIC-IIC indicated by arrows in FIG. 2A;

DESCRIPTION OF THE PREFERRED EMBODIMENTS

Figure 3A:
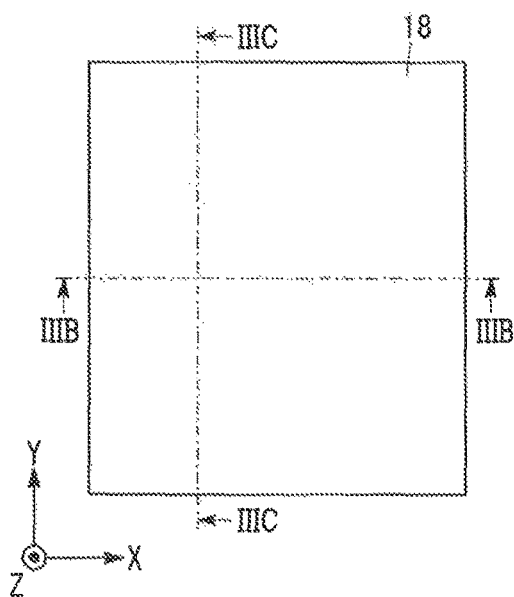
FIG. 3A is a plan view of a transmission membrane side of a first substrate having a transmission membrane on one surface thereof and a covering membrane precursor on the other surface.

Hereinafter, preferred embodiments of an analytical cell and a method of producing the analytical cell, according to the present invention, will be described in detail with reference to the accompanying drawings.

The analytical cell is suitable for use, e.g., in performing an analysis of electrode reactions in a negative electrode active material and a positive electrode active material by use of electron beam transmission in various types of analytical equipment. For example, the analytical equipment may be a transmission electron microscope (TEM). In this case, the analytical cell is accommodated in a front end of a holder, and an observation process is performed. Further, for example, the analytical cell may be any of a metal ion secondary cell of lithium, sodium, or the like, a nickel-hydrogen cell, an alkaline-manganese cell, a metal ion air cell, a metal ion all solid cell, etc., and a fuel cell such as a solid polymer electrolyte fuel cell. Hereinafter, examples of an analytical cell made up of a lithium ion secondary cell will be described.

An analytical cell 10 according to an embodiment of the present invention will be described with reference to FIGS. 1, 2A, 2B, and 2C. In the following description, for ease of understanding the invention, the X-axis, Y-axis, and Z-axis directions shown in the drawings are defined as width, depth, and height (thickness) directions, respectively. In addition, in the X-axis, Y-axis, and Z-axis directions, the tip of the arrow will be referred to as one end, and the base end of the arrow will be referred to as another end.

The analytical cell 10 includes a first substrate 12 and a second substrate 14. The first substrate 12 may be a substrate containing silicon (Si) having a silicon nitride ($Si_3N_4$) membrane or a substrate containing Si having an oxide covering membrane of $SiO_2$, etc., or a substrate containing borosilicate glass, quartz ($SiO_2$), or the like. Further, as shown in FIGS. 2A to 2C, a through hole 16 is formed in the first substrate 12 at a position slightly shifted from the center of the first substrate 12 in the width direction toward the one end thereof in the width direction. The through hole 16 extends through the first substrate 12 in the thickness direction. A transmission membrane 18 is provided on one surface of the first substrate 12 to cover the through hole 16, and a covering membrane 20 is provided on the other surface of the first substrate 12 in a manner to expose the through hole 16.

The through hole 16 has a truncated square pyramid shape which is tapered from the other surface of the first substrate 12 with the covering membrane 20 formed thereon toward the one surface thereof with the transmission membrane 18 formed thereon. The transmission membrane 18 is made of a material having an electron beam permeability (electron beam transparency) such as silicon nitride ($Si_3N_4$), silicon carbide (SiC), etc. The covering membrane 20 may be made of the same material as the transmission membrane 18.

The second substrate 14 is made of the same material, and has the same shape as the first substrate 12, except that a through hole 16 is formed in the second substrate 14 at a position slightly shifted from the center of the second substrate 14 in the width direction toward the other end thereof in the width direction. As in the case of the first substrate 12, the transmission membrane 18 is provided on one surface of the second substrate 14, and the covering membrane 20 is provided on the other surface of the second substrate 14.

The first substrate 12 and the second substrate 14 (hereinafter will be also collectively referred to as substrates) are partially overlapped with each other such that the surface of the first substrate 12 having the transmission membrane 18 and the surface of the second substrate 14 having the transmission membrane 18 face each other, to thereby form an overlapping portion 22. In the overlapping portion 22, the through holes 16 of the substrates 12, 14 face each other across the transmission membranes 18. Further, spacers 24 (see FIG. 2A) and solid state joints 26 (see FIGS. 2A and 2C) are present between the substrates 12, 14 to maintain a desired distance between the substrates 12, 14.

For example, the spacers 24 are provided at four corners of the overlapping portion 22, and each of the spacers 24 is made of electrically insulating material and has a rectangular parallelepiped shape. As described later, each of the spacers 24 comprises a stack body formed by a first spacer 28 (see FIGS. 6A and 6C) and a second spacer 30 (see FIGS. 9A and 9C) abutting with each other, the first spacer 28 protruding from the transmission membrane 18 of the first substrate 12, the second spacer 30 protruding from the transmission membrane 18 of the second substrate 14. It should be noted that the positions and shapes of the spacers 24 and the solid state joints 26 in the overlapping portion 22 are not limited to the above as long as the substrates 12, 14 can be spaced from each other by a predetermined distance by the spacers 24 and the solid state joints 26. For example, each of the spacers 24 is not limited to the stack body, and may have a single-body structure formed on one of the substrates 12, 14 and which has the same height as the stack body. Further, if the substrates 12, 14 can be spaced from each other by a desired distance without using the spacers 24, then the spacers 24 may not be provided.

A pair of the solid state joints 26 are provided at both ends of the overlapping portion 22 in the depth direction and extend along the width direction. The solid state joints 26 seal respective sides of the overlapping portion 22 extending in the width direction. Specially, each of the solid state joints 26 is formed by solid state bonding of a first solid portion 32 (see FIGS. 8A and 8C) and a second solid portion 34 (see FIGS. 9A and 9C), the first solid portion 32 protruding from the transmission membrane 18 of the first substrate 12, the second solid portion 34 protruding from the transmission membrane 18 of the second substrate 14. That is, owing to the presence of the solid state joints 26, the substrates 12, 14 are joined together in a state where the overlapping portion 22 is formed.

The material suitable for the first solid portion 32 and the second solid portion 34 forming the solid state joint 26 includes a metal such as gold (Au), copper (Cu), aluminum (Al), etc., or an inorganic material such as $SiO_2$, Si, etc. The material of the first solid portion 32 and the material of the second solid portion 34 may be the same, or may be different from each other. In the case where the first solid portion 32 and the second solid portion 34 are made of metal, as the solid state bonding, any of various methods, including hot pressure welding, cold pressure welding, diffusion welding, friction pressure welding, and the like may be adopted. Further, in the case where the first solid portion 32 and the second solid portion 34 are made of inorganic material, as an example of the solid state bonding, for example, a bonding method by bringing the bonding surfaces activated by surface treatment into contact with each other may be adopted. If such a method is adopted, it is not essential to apply any load for the bonding process.

Sides of the overlapping portion 22 extending in the depth direction at both ends in the width direction are sealed by sealants 27 (see FIGS. 2A and 2B) of epoxy-based resin adhesive, etc., while a space between the pair of solid state joints 26 is filled with electrolytic solution. It should be noted that the sealants 27 are omitted in FIG. 1. That is, in the analytical cell 10 according to the embodiment of the present invention, four sides of the overlapping portion 22 are sealed by the pair of solid state joints 26 and the sealants 27. In this structure, a liquid-tight space formed in the overlapping portion 22 contains electrolytic solution 36. Therefore, it is not required to flow the electrolytic solution 36 through the overlapping portion 22, and it is possible to reduce the pressure of the electrolytic solution 36 applied to the substrates 12, 14. Accordingly, it is possible to reduce the distance between the substrates 12, 14, and achieve size reduction of the analytical cell 10.

As the electrolytic solution 36, for example, it is possible to suitably use solution obtained by adding supporting electrolyte such as $LiPF_6$ of about 1M to propylene carbonate (PC), ethylene carbonate (EC), dimethyl carbonate (DMC), diethyl carbonate (DEC), ethyl methyl carbonate (EMC), vinylene carbonate (VC), etc.

In the overlapping portion 22, the through hole 16 of the first substrate 12 and the through hole 16 of the second substrate 14 are overlapped with (in alignment with) each other across the transmission membranes 18. In this regard, as described above, since the through holes 16 are shifted from the center, one end of the first substrate 12 in the width direction and the other end of the second substrate 14 in the width direction are exposed from the overlapping portion 22, respectively.

Further, an observation window 38 is formed between the through holes 16. Electron beams can be transmitted satisfactorily through the observation window 38. That is, in the analytical cell 10, a negative electrode active material 40 and a positive electrode active material 42 are arranged at a distance from each other while being in contact with the electrolytic solution 36 between the transmission membranes 18 in the observation window 38, so that the electrode reactions and the like are analyzed using the electron beam transmission through the observation window 38. In the following description, a region of the overlapping portion 22 exclusive of the observation window 38, i.e., a region where the substrates 12, 14 face each other across the transmission membranes 18, will be referred to as a facing portion.

The negative electrode active material 40 is provided on the transmission membrane 18 of the first substrate 12, and is in the form of a layer extending from the observation window 38 toward the other end side in the width direction in the facing portion. The material suitable for forming the negative electrode active material 40 includes, for example, Li or a Li alloy, $Li_4Ti_5O_{12}$, Si, Ge, Sn or a Sn alloy, Al or an Al alloy, a Si oxide, a Sn oxide, an Al oxide, carbon (C), etc.

The positive electrode active material 42 is provided on the transmission membrane 18 of the second substrate 14, and is in the form of a layer extending from the observation window 38 toward one end side in the width direction in the facing portion. The material suitable for forming the positive electrode active material 42 includes, for example, $LiCoO_2$, $LiMnO_2$, $LiMn_2O_4$, $LiNiO_2$, $LiFePO_4$, $Li_2FePO_4F$, $LiCo_{1/3}Ni_{1/3}Mn_{1/3}O_2$, $Li(Li_\alpha Ni_x Mn_y Co_z)O_2$, etc.

The negative electrode active material 40 and the positive electrode active material 42 are electrically connectable to the outside of the overlapping portion 22 through a negative electrode collector 44 and a positive electrode collector 46, respectively. That is, the negative electrode collector 44 is provided on the transmission membrane 18 of the first substrate 12, and one end of the negative electrode collector 44 in the width direction is electrically connected to the negative electrode active material 40 in the facing portion of the overlapping portion 22, and the other end of the negative electrode collector 44 in the width direction is exposed to the outside of the overlapping portion 22 to form an exposed portion 48. The material suitable for the negative electrode collector 44 includes tungsten (W), copper (Cu), stainless steel (SUS), carbon (C), etc.

The positive electrode collector 46 is provided on the transmission membrane 18 of the second substrate 14. The other end of the positive electrode collector 46 in the width direction is electrically connected to the positive electrode active material 42 in the facing portion of the overlapping portion 22, and one end of the positive electrode collector 46 in the width direction is exposed to the outside of the overlapping portion 22 to form an exposed portion 50. The material suitable for the positive electrode collector 46 includes gold (Au), platinum (Pt), carbon (C), aluminum (Al), etc.

Preferably, the negative electrode collector 44 and the positive electrode collector 46 excluding the exposed portions 48, 50 are covered by an electrically insulating membrane 52. In this structure, contact of the negative electrode collector 44 and the positive electrode collector 46 with the electrolytic solution 36 can be blocked by the insulating membrane 52. Therefore, occurrence of side reactions in the negative electrode collector 44 and the positive electrode collector 46, different from the electrode reactions in the negative electrode active material 40 and the positive electrode active material 42 can be suppressed. Consequently, it becomes possible to analyze only the electrode reactions as the analysis subjects, highly accurately.

The analytical cell 10 basically has the structure as described above. For example, in the TEM observation of the analytical cell 10, firstly, the analytical cell 10 is placed on the holder in such a manner that the observation window 38 faces an electron beam irradiation part of the TEM. Then, the exposed portions 48, 50 are electrically connected to the charge-discharge tester or the like, through an electrical path provided in the holder to cause the electrode reactions as the observation subjects in the negative electrode active material 40 and the positive electrode active material 42.

The analytical cell 10 may be produced by a known semiconductor process (see, e.g., International Publication No. WO 2008/141147). Hereinafter, a method of producing the analytical cell 10 according to the embodiment of the present invention will be described below with reference to FIGS. 3A to 10C. It is a matter of course that the method of producing the analytical cell 10, and the order of steps for production of the analytical cell 10 are not limited to those described in the following description. In this example, the first substrate 12, the second substrate 14, and the negative electrode active material 40 are made of silicon (Si), the positive electrode active material 42 is made of lithium cobaltate ($LiCoO_2$), the transmission membrane 18 and the covering membrane 20 are made of silicon nitride ($Si_3N_4$), and the negative electrode collector 44 and the positive electrode collector 46 are made of tungsten (W).

As described above, the first solid portion 32 and the second solid portion 34 are provided separately and respectively on the first substrate 12 and the second substrate 14, and the first solid portion 32 and the second solid portion 34 are bonded together by solid state bonding to thereby form the overlapping portion 22, whereby the analytical cell 10 is obtained. Then, at the outset, steps of providing the constituent elements including the first solid portion 32 on the first substrate 12 will be described.

Figure 3C:
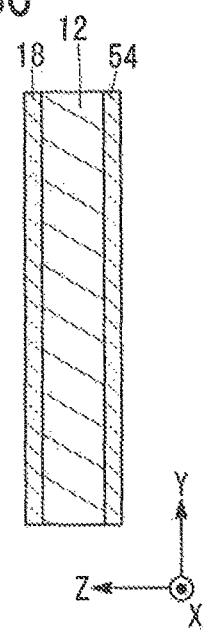
FIG. 3C is a cross sectional view taken along a line IIIC-IIIC indicated by arrows in FIG. 3A.
Figure 3B:
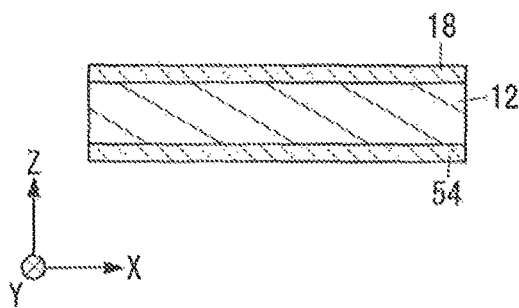
FIG. 3B is a cross sectional view taken along a line IIIB-IIIB indicated by arrows in FIG. 3A.

Firstly, as shown in FIGS. 3A to 3C, both surfaces of the first substrate 12 are polished, and each of the surfaces of the first substrate 12 is covered with a silicon nitride membrane by chemical vapor deposition (CVD). The silicon nitride membrane formed on the one surface of the first substrate 12 is used as the transmission membrane 18, and the silicon nitride membrane formed on the other surface is used as a precursor (covering membrane precursor 54) of the covering membrane 20.

Next, the transmission membrane 18 of the first substrate 12 is covered with a photoresist (not shown). A photolithography process is performed for removing the photoresist on portions where the negative electrode collector 44 and the first spacer 28 should be formed. In the process, in the transmission membrane 18, only the portions where the negative electrode collector 44 and the first spacer 28 should be formed are exposed.

Figure 4A:
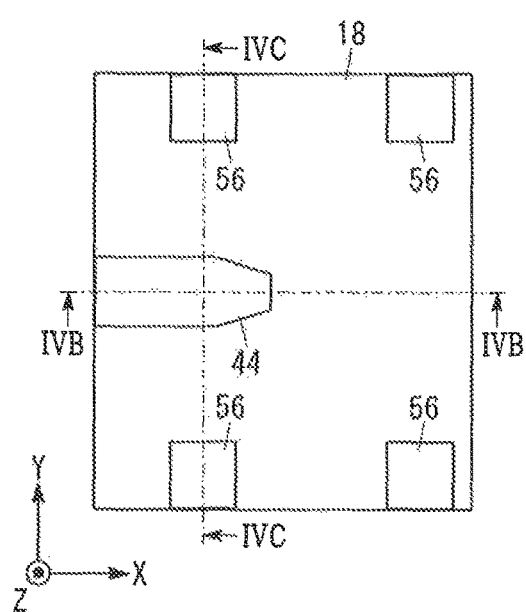
FIG. 4A is a plan view showing a state where a negative electrode collector and a spacer are provided on one surface of the first substrate in FIG. 3A.
Figure 4C:
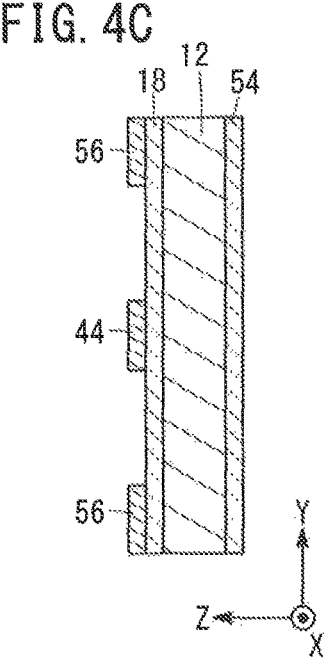
FIG. 4C is a cross sectional view taken along a line IVC-IVC indicated by arrows in FIG. 4A.
Figure 4B:
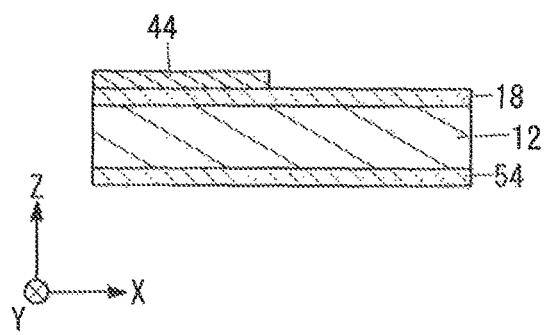
FIG. 4B is a cross sectional view taken along a line indicated by arrows IVB-IVB in FIG. 4A.

Next, the one surface of the first substrate 12 (the remaining photoresist and the exposed portions of the transmission membrane 18) are covered with a tungsten membrane by physical vapor deposition (PVD) such as vacuum deposition, and thereafter, the entire photoresist is removed (by lift-off processing). As a result, as shown in FIGS. 4A to 4C, the negative electrode collector 44 and the precursor of the first spacer 28 (spacer precursor 56), which are made up of the tungsten membrane, are formed on the transmission membrane 18 of the first substrate 12.

Next, the one surface of the first substrate 12 (the transmission membrane 18, the negative electrode collector 44, and the spacer precursor 56) is covered with a photoresist. A photolithography process is performed for removing the photoresist on a portion where the negative electrode active material 40 should be formed. In the process, in the transmission membrane 18 and the negative electrode collector 44, only the portion where the negative electrode active material 40 should be formed is exposed.

Figure 5A:
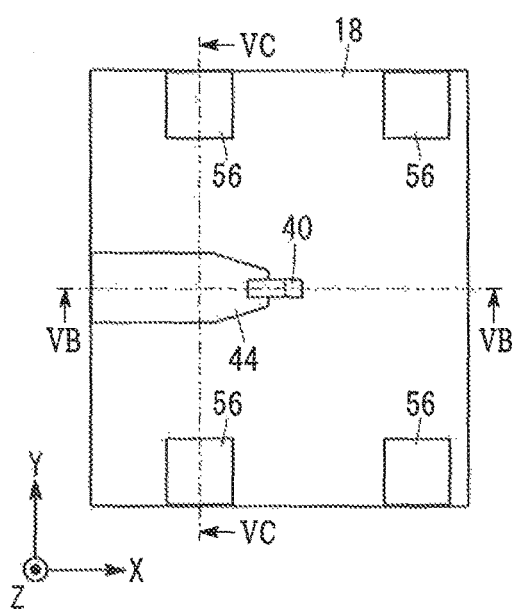
FIG. 5A is a plan view showing a state where negative electrode active material is provided on one surface of the first substrate in FIG. 4A.
Figure 5C:
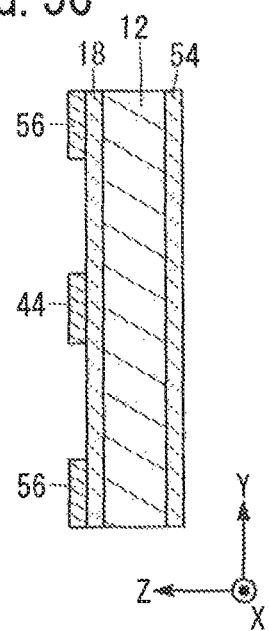
FIG. 5C is a cross sectional view taken along a line VC-VC indicated by arrows in FIG. 5A.
Figure 5B:
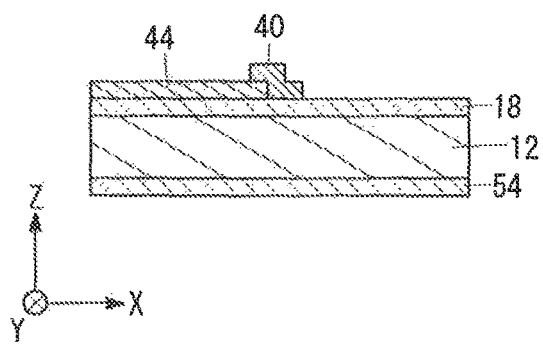
FIG. 5B is a cross sectional view taken along a line VB-VB indicated by arrows in FIG. 5A.

Next, by radio frequency spattering (RF spattering), the one surface of the first substrate 12 (the remaining photoresist, and the exposed portion of the transmission membrane 18 and the negative electrode collector 44) is covered with a silicon membrane. Then, the entire photoresist is removed. In this manner, as shown in FIGS. 5A to 5C, the negative electrode active material 40 of the silicon membrane is formed additionally on the transmission membrane 18 of the first substrate 12.

Next, the one surface of the first substrate 12 (the transmission membrane 18, the negative electrode collector 44, the spacer precursor 56, and the negative electrode active material 40) is covered with a silicon nitride membrane by chemical vapor deposition (CVD). Then, this silicon nitride membrane is covered with a photoresist, and a photolithography process is performed. As a result of this process, the photoresist is left only on portions of the silicon nitride membrane that cover the negative electrode collector 44 excluding the exposed portion 48 and the spacer precursor 56.

Figure 6A:
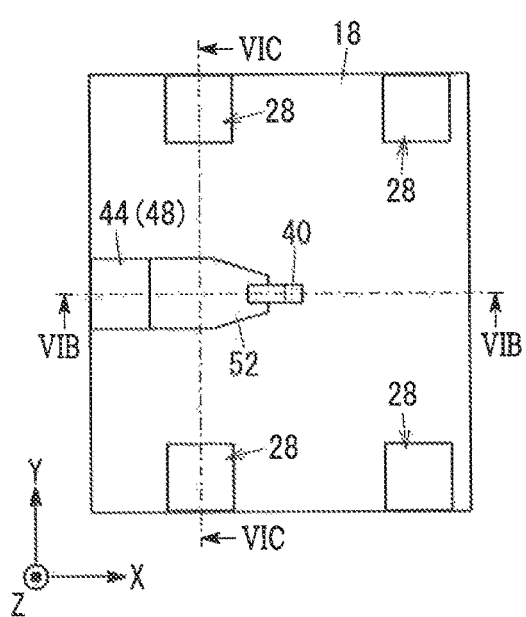
FIG. 6A is a plan view showing a state where, in one surface of the first substrate in FIG. 5A, a portion of the negative electrode collector excluding an exposed portion thereof and a spacer are covered with a silicon nitride membrane.
Figure 6C:
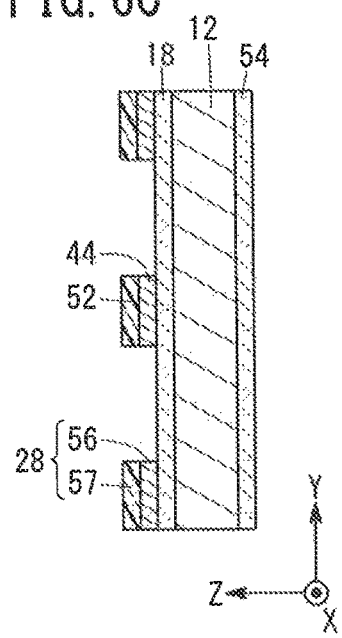
FIG. 6C is a cross sectional view taken along a line VIC-VIC indicated by arrows in FIG. 6A.
Figure 6B:
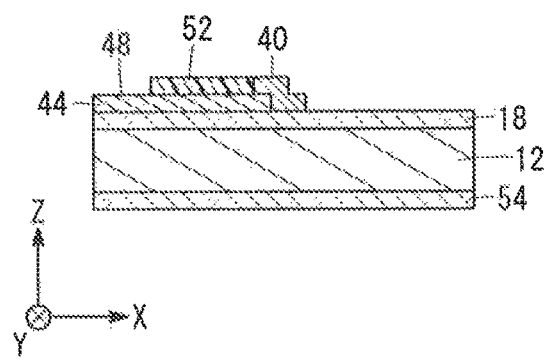
FIG. 6B is a cross sectional view taken along a line VIB-VIB indicated by arrows in FIG. 6A.

Next, for example, a dry etching process such as a reactive ion etching process is carried out using the remaining photoresist as a mask. In this process, the silicon nitride membrane covering the negative electrode collector 44 except the exposed portion 48 and the spacer precursor 56 are protected by the remaining photoresist. Thereafter, the entire photoresist is removed. Consequently, as shown in FIGS. 6A to 6C, the silicon nitride membrane covering the negative electrode collector 44 excluding the exposed portion 48 and the spacer precursor 56 is formed. The portion of the silicon nitride membrane covering the negative electrode collector 44 excluding the exposed portion 48 forms the insulating membrane 52, and the silicon nitride membrane 57 covering the spacer precursor 56 and the spacer precursor 56 jointly form the first spacer 28.

Next, the one surface of the first substrate 12 (the transmission membrane 18, the negative electrode collector 44, the first spacer 28, the negative electrode active material 40, and the insulating membrane 52) is covered with a photoresist, and a photolithography process is performed. In the photolithography process, the photoresist on a portion where the first solid portion 32 should be formed is removed. As a result, only the portion of the transmission membrane 18 where the first solid portion 32 should be formed as described later is exposed. In this regard, the thickness of the photoresist should be determined to have substantially the same value as a desired length by which the first solid portion 32 protrudes.

Figure 7A:
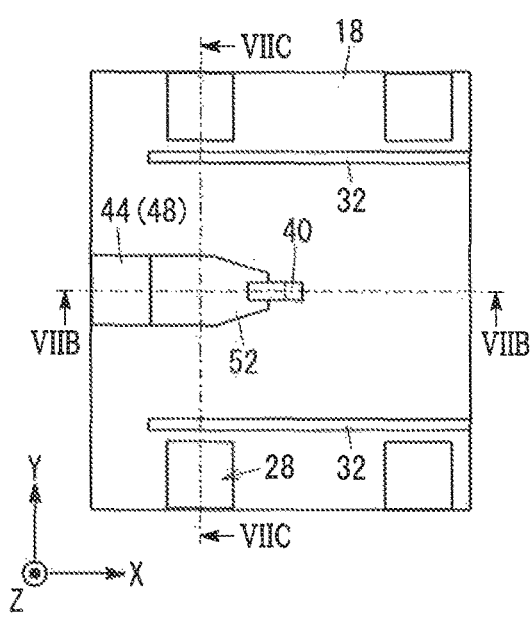
FIG. 7A is a plan view showing a state where a first solid portion is provided on one surface of the first substrate in FIG. 6A.
Figure 7C:
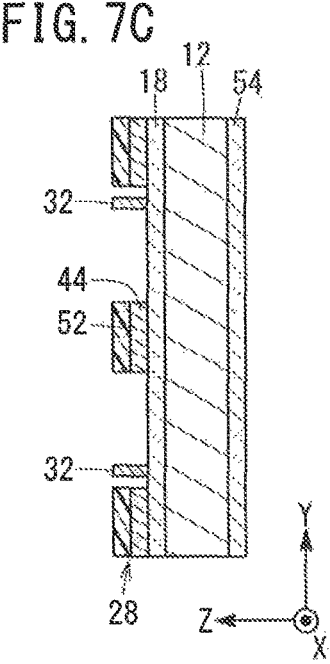
FIG. 7C is a cross sectional view taken along a line indicated by arrows VIIC-VIIC in FIG. 7A.
Figure 7B:
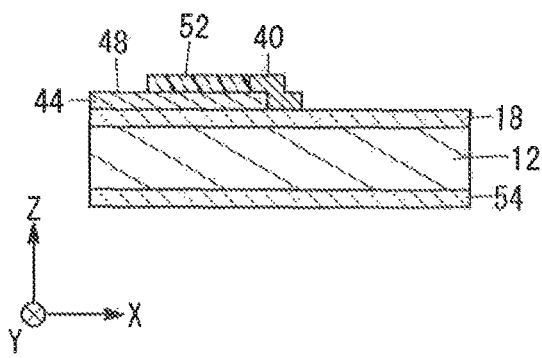
FIG. 7B is a cross sectional view taken along a line indicated by arrows VIIB-VIIB in FIG. 7A.

Next, using the PVD method, the one surface of the first substrate 12 (the remaining photoresist and the exposed portion of the transmission membrane 18) is covered with a gold membrane. Thereafter, the entire photoresist is removed. Consequently, as shown in FIGS. 7A to 7C, the first solid portion 32 of the gold membrane is formed on the transmission membrane 18 of the first substrate 12. It should be noted that the height of the first spacer 28 and the height of the first solid portion 32 may be the same, or the first spacer 28 may be slightly lower than the first solid portion 32.

Next, with respect to the other surface of the first substrate 12, a covering membrane precursor 54 is covered with a photoresist, and a photolithography process is performed. In the process, the photoresist is partly removed so as to expose a portion of the covering membrane precursor 54 that lies in a region where the through hole 16 of the first substrate 12 should be formed.

Next, a dry etching process is carried out using the remaining photoresist as a mask. As a result, only a portion of the covering membrane precursor 54 that is exposed from the photoresist is removed from among the entire covering membrane precursor 54 on the first substrate 12. In this manner, after removing the portion of the covering membrane precursor 54 where the through hole 16 should be formed in the first substrate 12, by removing the entire photoresist, the covering membrane 20 is obtained.

Figure 8A:
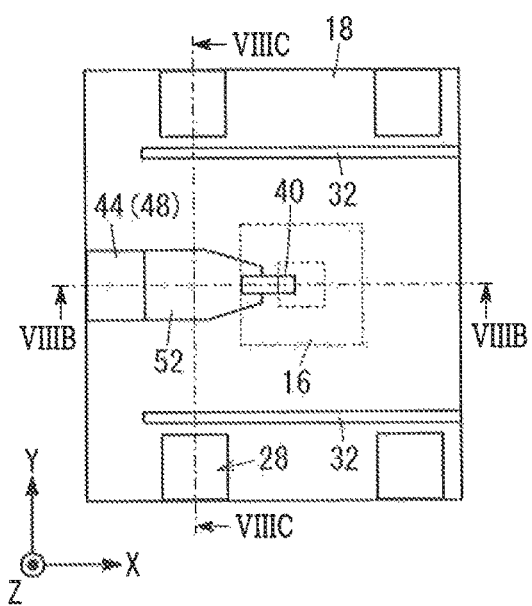
FIG. 8A is a plan view showing a state where a covering membrane and a through hole are formed in the first substrate in FIG. 7A.
Figure 8C:
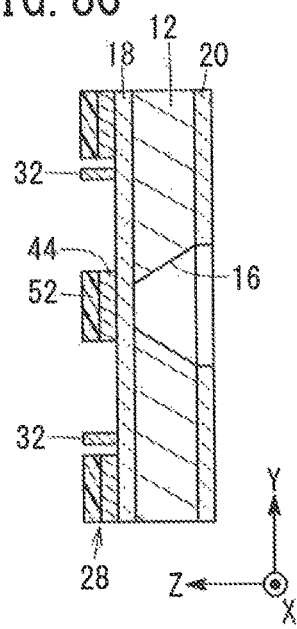
FIG. 8C is a cross sectional view taken along a line VIIIC-VIIIC indicated by arrows in FIG. 8A.
Figure 8B:
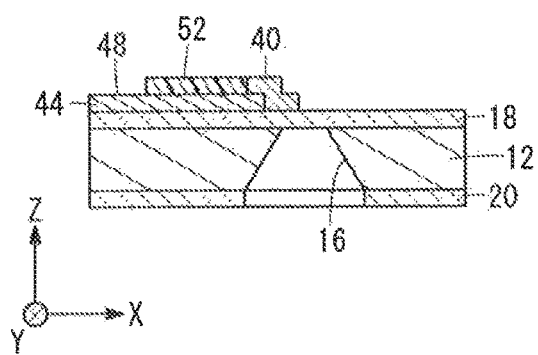
FIG. 8B is a cross sectional view taken along a line VIIIB-VIIIB indicated by arrows in FIG. 8A.

Next, as shown in FIGS. 8A to 8C, a wet etching process (through-hole etching) is applied to the other surface of the first substrate 12 to form the through hole 16. In this manner, the through hole 16 is formed in the first substrate 12 such that one end of the through hole 16 is covered with the transmission membrane 18 disposed on the one surface side of the first substrate 12. Incidentally, the one surface of the first substrate 12 may be covered with an alkali-resistant surface protection layer (not shown) before performing the wet etching process. In this case, the one surface of the first substrate 12 can be protected by the alkali-resistant surface protection layer. The alkali-resistant surface protection layer should be removed by dry etching or by using a remover liquid after forming the through hole 16 as described above.

Figure 9A:
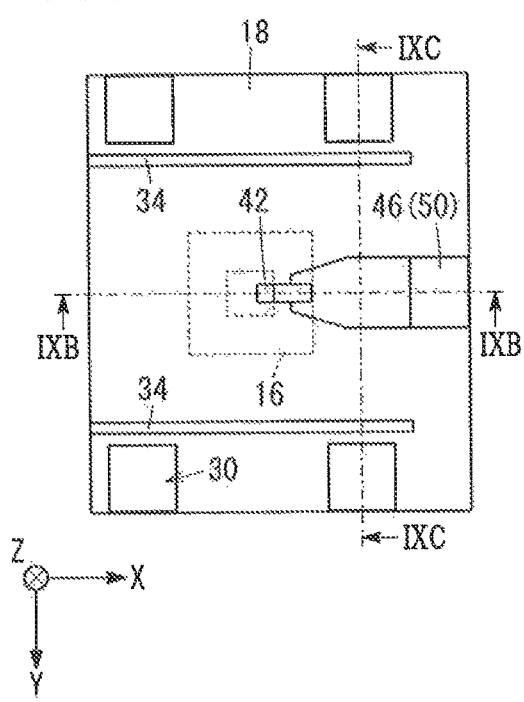
FIG. 9A is a plan view of a second substrate having a transmission membrane, a positive electrode collector, a spacer, a positive electrode active material, an insulating membrane, a second solid portion, a covering membrane, and a through hole that are provided in the same manner as in the case of the first substrate in FIG. 8A.
Figure 9C:
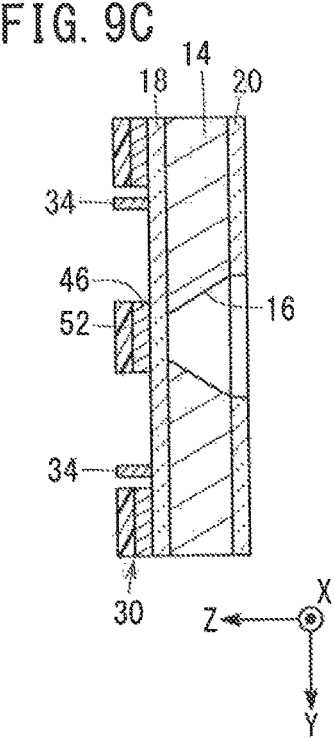
FIG. 9C is a cross sectional view taken along a line IXC-IXC indicated by arrows in FIG. 9A.
Figure 9B:
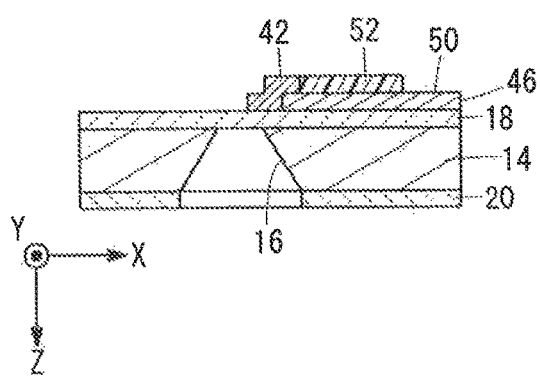
FIG. 9B is a cross sectional view taken along a line IXB-IXB indicated by arrows in FIG. 9A.

Also with respect to the second substrate 14, by carrying out the same processes as in the case of the first substrate 12, as shown in FIGS. 9A to 9C, it is possible to form, on the second substrate 14, the transmission membrane 18, the positive electrode collector 46, the insulating membrane 52, the positive electrode active material 42, the second spacer 30, the second solid portion 34, the covering membrane 20, and the through hole 16. In order to improve the activity of the positive electrode active material 42, annealing treatment for enhancing the crystallinity of the positive electrode active material 42 may be applied, or the membrane thickness or the shape pattern of the positive electrode active material 42 may be changed.

Figure 10A:
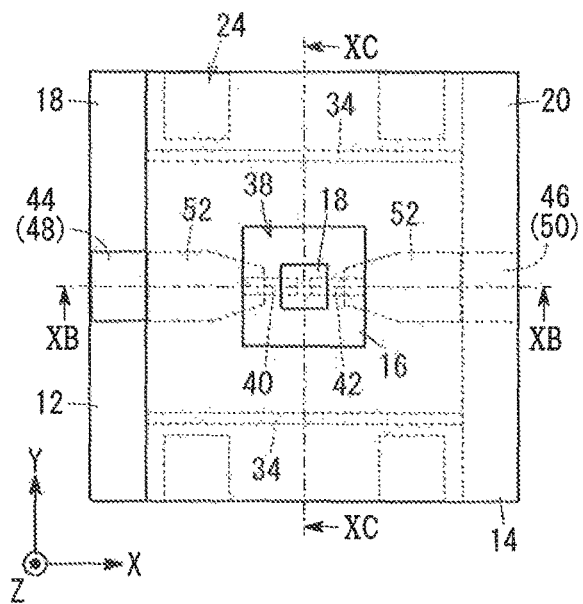
FIG. 10A is a plan view showing a state where the first solid portion of the first substrate in FIG. 8A and the second solid portion of the second substrate in FIG. 9A are in abutment with each other.
Figure 10C:
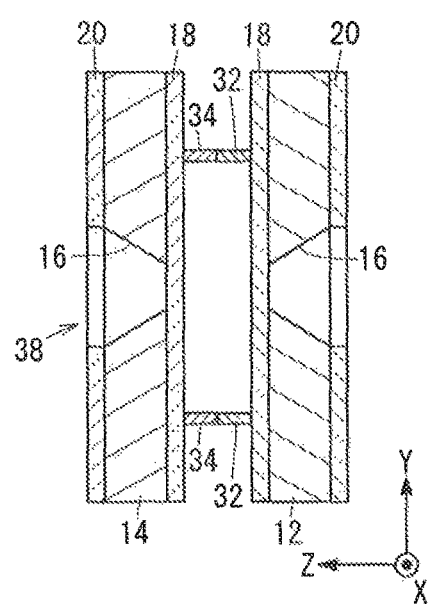
FIG. 10C is a cross sectional view taken along a line XC-XC indicated by arrows in FIG. 10A.
Figure 10B:
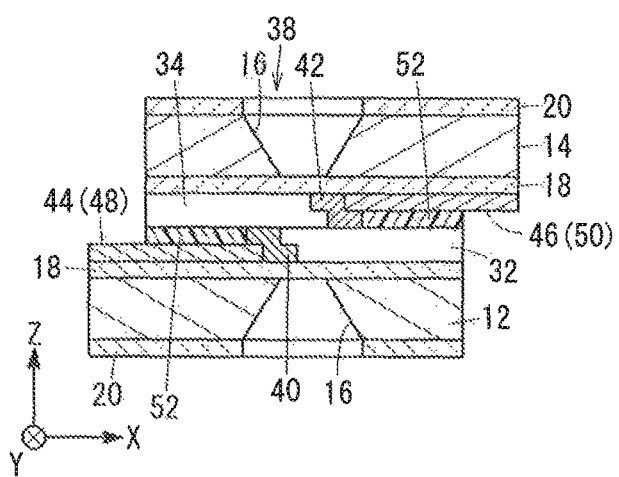
FIG. 10B is a cross sectional view taken along a line XB-XB indicated by arrows in FIG. 10A.

Next, as shown in FIGS. 10A to 10C, the first substrate 12 and the second substrate 14 are partially overlapped with each other, and the first substrate 12 and the second substrate 14 are positioned in such a manner that the through hole 16 of the first substrate 12 and the through hole 16 of the second substrate 14 are arranged face-to-face with each other across the transmission membranes 18. In this state, the first solid portion 32 and the second solid portion 34 are brought into abutment against each other. That is, the first solid portion 32 and the second solid portion 34 protrude respectively on portions of the first substrate 12 and the second substrate 14 that are face-to-face with each other when the substrates 12, 14 are mutually positioned in the above manner. Further, the first spacer 28 and the second spacer 30 are provided respectively on the first substrate 12 and the second substrate 14 such that the first and second spacer are stacked together to form the spacer 24.

In order to suppress variations in the contact area when the first solid portion 32 and the second solid portion 34 contact each other, preferably, the length of the first solid portion 32 in the depth direction and the length of the second solid portion 34 in the depth direction are different from each other. In this manner, as described later, at the time of applying a pressure load to the contact area between the first solid portion 32 and the second solid portion 34, it is possible to suppress variations in the pressure, and improve the uniformity of bonding by the solid state joint.

Figure 11A:
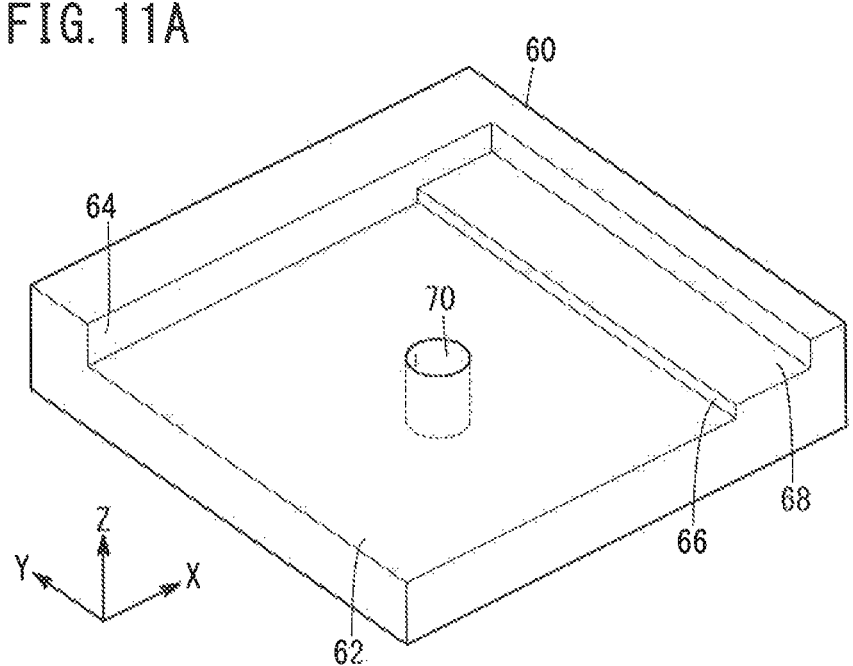
FIG. 11A is a perspective view of a jig used at the time of positioning the first substrate and the second substrate.
Figure 11B:
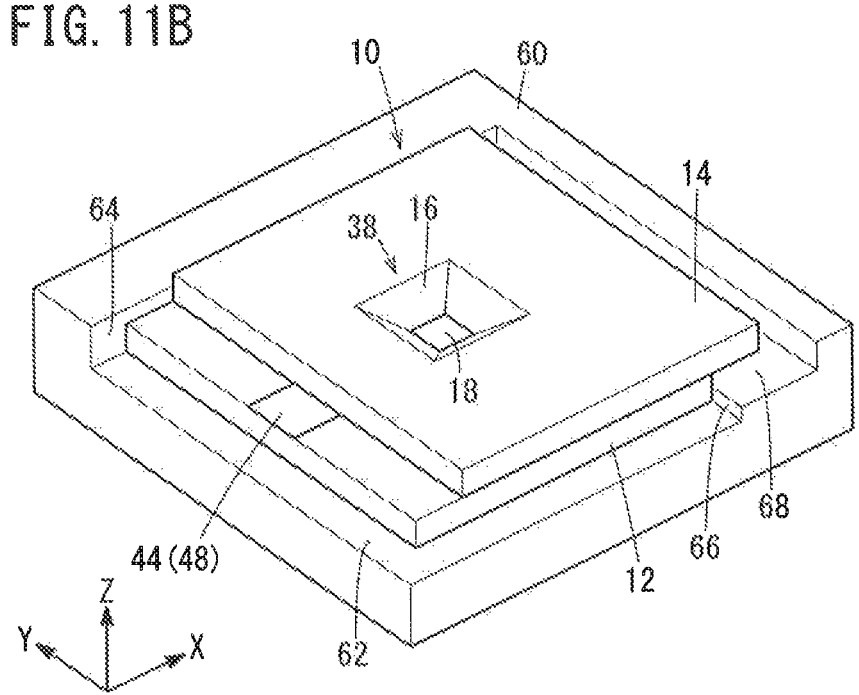
FIG. 11B is a perspective view showing a state where the first substrate and the second substrate are provided on the jig in FIG. 11A.

For example, a jig 60 shown in FIGS. 11A and 11B may be used for performing the above positioning operation more easily with a higher degree of accuracy. The jig 60 may be made of stainless steel (SUS), etc., and includes a first placement surface 62, a first side wall 64, a second side wall 66, and a second placement surface 68. A through hole 70 is formed at substantially the center of the first placement surface 62.

The height of the first side wall 64 extending upright from the first placement surface 62 is larger than the thickness of the first substrate 12, and slightly smaller than the height of the overlapping portion 22. The second side wall 66 is perpendicular to both of the first placement surface 62 and the first side wall 64, and forms a step between the first placement surface 62 and the second placement surface 68. The height of this second side wall 66 is smaller than the thickness of the first substrate 12.

In the case of positioning the substrates 12, 14 with respect to each other using this jig 60, firstly, the jig 60 is placed on a sample stage of an optical microscope in such a manner that light is radiated from under the through hole 70. Next, the other surface of the first substrate 12 is placed on the first placement surface 62. At this time, a side surface of the first substrate 12 on one end side in the depth direction is brought into abutment against the first side wall 64, and another side surface of the first substrate 12 on one end side in the width direction is brought into abutment against the second side wall 66. Next, the second substrate 14 is overlapped with the first substrate 12 such that one surface of the first substrate 12 and one surface of the second substrate 14 face each other. In this regard, in a state where a side surface of the second substrate 14 on one end side in the depth direction abuts against the first side wall 64, by sliding the second substrate 14 in the width direction indicated by an arrow X, the position of the second substrate 14 is adjusted in such a manner that the through hole 16 of the first substrate 12 and the through hole 16 of the second substrate 14 are arranged face-to-face with each other in the field of view of the optical microscope. Thus, it is possible to form the overlapping portion 22 by positioning the substrates 12, 14 in such a manner that the through hole 16 of the first substrate 12 and the through hole 16 of the second substrate 14 face each other, and the first solid portion 32 and the second solid portion 34 abut against each other.

That is, the dimensions of the jig 60 are set (determined) such that the positioning operation can be performed by placing the substrates 12, 14 in the manner as described above. Accordingly, using this jig 60, it is possible to position the substrates 12, 14 with each other easily with a high degree of accuracy. Further, for example, using a fixing means (not shown) made of SUS, etc., it is possible to fix the substrates 12, 14 positioned as described above, to the jig 60. In this manner, since it is possible to maintain a state where the bonding surface of the first solid portion 32 and the bonding surface of the second solid portion 34 are placed into abutment against each other, the solid state bonding can be performed easily.

In the embodiment where the first solid portion 32 and the second solid portion 34 are made of gold, as described above, the bonding surface of the first solid portion 32 and the bonding surface of the second solid portion 34 are brought into abutment against each other. In this state, a pressure load in a range of 0.2 to 2.0 kgf per the unit bonding area of 1 mm$^2$ may be applied to the first solid portion 32 and the second solid portion 34, e.g., at temperature in a range of 300 to 400° C., preferably at temperature of 400° C. for 15 to 60 minutes. In this manner, solid state bonding of the first solid portion 32 and the second solid portion 34 is performed firmly to thereby obtain the solid state joint 26.

In the case where the first solid portion 32 and the second solid portion 34 are made of aluminum, the same load as described above should be applied at temperature in a range of 400 to 450° C., preferably at temperature of 400° C., for the same time period as described above. Alternatively, in the case where the first solid portion 32 and the second solid portion 34 are made of copper, the same load as described above should be applied at temperature in a range of 350 to 450° C., preferably at temperature of 350° C., for the same time period as described above.

Further, in the case where the first solid portion 32 and the second solid portion 34 are made of inorganic material, the bonding surfaces of the first solid portion 32 and the second solid portion 34 may be activated before formation of the overlapping portion 22. Such activation of the bonding surfaces can be performed using existing devices such as a room-temperature wafer bonder "BOND MEISTER" (product name) of Mitsubishi Heavy Industries, Ltd., a surface activation wafer bonding kit (Model type: WP-100) of PMT Corporation, etc.

More specifically, sputter etching using ion beams, plasma, etc. may be applied to each of the bonding surfaces in a vacuum chamber at room temperature under high vacuum. In this manner, it is possible to remove an oxide film and adsorption films comprising water, organic material, etc., formed on the bonding surfaces to thereby expose atoms having bonds, i.e., activate the bonding surfaces. If the bonding surfaces activated in this manner are brought into contact with each other, since a bonding force is generated between the bonding surfaces, it is possible to obtain the solid state joint 26 formed by firm solid state bonding of the first solid portion 32 and the second solid portion 34. The bonding conditions in this process should be determined appropriately based on the material, shape, or the like of the first solid portion 32 and the second solid portion 34.

By forming the solid state joint 26 by the above solid state bonding, it is possible to obtain the overlapping portion 22 by joining the substrates 12, 14 together in a state where the substrates 12, 14 are positioned with each other in the manner as described above, and ensure that the substrates 12, 14 are spaced from each other by a distance depending on the height of the solid state joint 26.

That is, since the substrates 12, 14 can be mutually positioned without using any holders, etc. for holding the analytical cell 10 in the analytical equipment, it is possible to position the substrates 12, 14 with respect to each other easily with a high degree of accuracy regardless of the machining precision, etc., of the holder.

Further, the height of the solid state joint 26 formed by solid state bonding without melting the first solid portion 32 and the second solid portion 34 is substantially the same as the total value of the height of the first solid portion 32 and the height of the second solid portion 34. That is, by adjusting the height of the first solid portion 32 and the height of the second solid portion 34, it is possible to set the distance between the substrates 12, 14 easily.

The analytical cell 10 can be obtained by providing the sealants 27 in a state where a space within the overlapping portion 22 formed as described above is filled with the electrolytic solution 36. In this regard, as described above, since the two sides of the overlapping portion 22 extending in the width direction are sealed by the solid state joints 26, the liquid-tight space can be formed simply by providing the sealants 27 so as to seal the other two sides of the overlapping portion 22 extending in the depth direction. Thus, it becomes possible to simplify the production steps to thereby obtain the analytical cell 10 efficiently.

Further, since the substrates 12, 14 of the analytical cell 10 are joined together by the solid state joints 26, at the time of attaching the analytical cell 10 to the holder, and performing observation using the electron microscope in a high vacuum atmosphere, it is possible to suppress positional displacement between the substrates 12, 14 and occurrence of changes in the distance between the substrates 12, 14.

As described above, in the analytical cell 10, since it is possible to position the substrates 12, 14 with respect to each other, and set and maintain the distance between the substrates 12, 14 easily with a high degree of accuracy, i.e., since it is possible to form and maintain the observation window 38 with a high degree of accuracy, it is possible to observe the electrode reactions, etc. accurately through the observation window 38.

The present invention is not limited to the embodiments described above, and various modifications can be made without deviating from the scope of the present invention as defined by the appended claims.

For example, in the analytical cell 10 according to the above embodiment, the negative electrode active material 40 is provided on the first substrate 12, and the positive electrode active material 42 is provided on the second substrate 14. In this manner, by providing the negative electrode active material 40 and the positive electrode active material 42 on the separate substrates 12, 14, it is possible to prevent the negative electrode active material 40 and the positive electrode active material 42 from being positioned excessively close to each other, or contacting each other. Therefore, even if the space for providing the negative electrode active material 40 and the positive electrode active material 42 is small, since short circuiting between the negative electrode active material 40 and the positive electrode active material 42 can be prevented effectively, it becomes possible to reduce the size of the analytical cell 10 even more effectively.

However, the present invention is not limited to the above structure. For example, both of the negative electrode active material 40 and the positive electrode active material 42 may be provided on one of the first substrate 12 and the second substrate 14. In this case, the width of the one substrate where the negative electrode active material 40 and the positive electrode active material 42 are provided is larger than the width of the other substrate. In this manner, since both ends of the one substrate in the width direction can be exposed from the overlapping portion with the other substrate, it is possible to provide the exposed portions 48, 50 on the negative electrode collector 44 and the positive electrode collector 46, respectively. In such structure, the step of providing the negative electrode active material 40, the positive electrode active material 42, the negative electrode collector 44, the positive electrode collector 46, the insulating membrane 52, etc. only has to be performed on one of the substrates. Therefore, it becomes possible to obtain the analytical cell by simple production steps easily and efficiently.

Further, even in the case where the analytical cell 10 does not use the jig 60, the operations of positioning and solid state bonding can be performed easily. This is because, as described above, at the time of assembling the analytical cell 10, since there is no need to accommodate the substrates 12, 14 in a pocket, etc. of the holder, it is possible to perform the positioning operation by making adjustment easily such that the edge of the through hole 16 formed in the first substrate 12 and the edge of the through hole 16 formed in the second substrate 14 are overlapped with each other in a plan view.

Furthermore, in the case where the analytical cell 10 or the like of the above embodiment is not the lithium-ion secondary cell but the nickel-hydrogen cell, for example, a positive electrode of nickel hydroxide, a negative electrode of any of various hydrogen storing alloys, and an electrolytic solution of aqueous potassium hydroxide solution (KOH (aq)) may be used. Alternatively, in the case where the analytical cell 10 is the alkaline manganese cell, for example, a positive electrode of manganese dioxide/graphite, a negative electrode of zinc, and an electrolytic solution of KOH(aq) may be used.

Further, The analytical cell 10 can be used in an analysis not only by the TEM but also by any general analytical equipment using an electron beam.

Using the above steps, a test specimen of the analytical cell according to the embodiment was prepared. Specifically, as the first substrate 12 and the second substrate 14, silicon substrates having a width of 3 mm, a depth of 2.5 mm, and a thickness of 200 µm were selected. A through hole 16 having a width of 60 µm and a depth of 60 µm was formed in each of the silicon substrates. With respect to the first substrate 12, a transmission membrane 18 made of a silicon nitride membrane having a thickness of 80 nm, a negative electrode collector 44 made of a tungsten membrane having a thickness of 100 nm, a negative electrode active material 40 made of silicon, an insulating membrane 52 made of a silicon nitride membrane, a first spacer 28 formed by stacking a tungsten membrane and a silicon nitride membrane to have the total thickness of 250 nm, and a first solid portion 32 made of a thin gold membrane having a width of 2 mm, a depth of 0.10 mm, and a thickness of 300 nm were formed.

Further, with respect to the second substrate 14, a transmission membrane 18 made of a silicon nitride membrane having a thickness of 80 nm, a positive electrode collector 46 made of a tungsten membrane having a thickness of 100 nm, a positive electrode active material 42 made of lithium cobaltate, an insulating membrane 52 made of a silicon nitride membrane, a second spacer 30 formed by stacking a tungsten membrane and a silicon nitride membrane to have the total thickness of 250 nm, and a second solid portion 34 made of a thin gold membrane having a width of 2 mm, a depth of 0.15 mm, and a thickness of 300 nm were formed.

Therefore, the bonding area for solid state bonding of the first solid portion 32 and the second solid portion 34 is calculated as follows: 2 mm×0.10 mm×two areas=0.4 mm$^2$. The setting value of the height of the solid state joint 26 obtained by this solid state bonding process is 600 nm. That is, in the test specimen of the analytical cell of the embodiment, the target setting value of the distance between the substrates 12, 14 was 600 nm.

Next, using the jig 60, the first substrate 12 and the second substrate 14 were positioned in the manner as described above. In this process, the through hole 16 of the substrate 12 and the through hole 16 of the substrate 14 were positioned to face each other across the transmission membranes 18 to form the observation window 38.

Next, using the fixing means, while abutment of the bonding surfaces of the first solid portion 32 and the second solid portion 34 against each other was maintained, solid state bonding was performed by applying a load of 400 g at 300° C. for 30 minutes. That is, a load of 1 kgf per the unit bonding area of 1 mm$^2$ was applied to form the solid state joint 26. In this manner, a test specimen of the analytical cell according to the embodiment was obtained.

In the test specimen of this analytical cell, the first substrate 12 and the second substrate 14 were joined together using the solid state joints 26. It was confirmed that the state where the first substrate 12 and the second substrate 14 were positioned in the manner as described above was maintained suitably. Further, it was confirmed that the distance between the substrates 12, 14 was 585 nm and that the actual distance was substantially equal to the target setting value. That is, by setting the heights of the first solid portion 32 and the second solid portion 34, it was possible to easily set the height of the solid state joint 26, i.e., the distance between the substrates 12, 14 to a desired value easily.

What is claimed is:

1. An analytical cell comprising a first substrate and a second substrate which are partially overlapped with each other to form an overlapping portion, the overlapping portion being configured to allow electrolytic solution to be present between the first substrate and the second substrate, an observation window being formed in the overlapping portion, an electron beam being transmittable through the observation window,
   wherein the first substrate and the second substrate have respective through holes extending therethrough in a thickness direction thereof, and also have respective transmission membranes having an electron beam permeability, the transmission membranes being disposed on respective surfaces of the first substrate and the second substrate so as to cover ends of the respective through holes which face each other;
   in the overlapping portion, a solid state joint is provided in which a first solid portion protruding from the first substrate and a second solid portion protruding from the second substrate are connected together so that the first substrate and the second substrate are fixed and maintained in position relative to each other by the solid state joint, surfaces of the substrates are spaced from each other by a predetermined distance, and the substrates are positioned to form the observation window at a position where the through hole of the first substrate and the through hole of the second substrate face each other across the transmission membranes;
   in a space within the overlapping portion, a negative electrode active material and a positive electrode active material are provided, and the negative electrode active material and the positive electrode active material are spaced from each other so that when the electrolytic solution is present the electrode active materials contact the electrolytic solution individually; and
   a negative electrode collector and a positive electrode collector extend from an inside of the overlapping portion to an outside thereof so as to be exposed to the outside, and the negative electrode collector and the positive electrode collector are electrically connected respectively to the negative electrode active material and the positive electrode active material inside the overlapping portion.

2. The analytical cell according to claim 1, wherein the solid state joint is provided to seal at least one side of the overlapping portion.

3. The analytical cell according to claim 1, further comprising sealant which forms a seal between portions of the first and second substrates at the overlapping portion, wherein the solid state joint also forms a seal between other portions of the first and second substrates at the overlapping portion, and the sealant and the solid state joint together define a liquid-tight space in the overlapping portion in which the electrolytic solution is contained such that the electrolytic solution does not flow.

4. The analytical cell according to claim 1, further comprising electrically insulating members which respectively cover the negative electrode collector and the positive electrode collector to prevent side reactions from occurring in the electrode collectors.

5. A method of producing the analytical cell according to claim 1 comprising the first substrate and the second substrate which are partially overlapped with each other to form the overlapping portion, the overlapping portion being configured to allow electrolytic solution to be present between the first substrate and the second substrate, the observation window being formed in the overlapping portion at the position where the through hole of the first substrate and the through hole of the second substrate face each other, the electron beam being transmittable through the observation window,
   the method comprising the steps of:
   forming the first solid portion protruding from the first substrate and forming the second solid portion protruding from the second substrate, wherein the first solid portion and the second solid portion are formed respectively on portions of the first substrate and the second substrate that are face-to-face with each other when the first substrate and the second substrate are positioned to form the overlapping portion,
   positioning the first substrate and the second substrate to bring the first solid portion and the second solid portion into abutment against each other; and
   forming the solid state joint by solid state bonding of the first solid portion and the second solid portion that are in abutment against each other, so that the first substrate and the second substrate are fixed and maintained in position relative to each other by the solid state joint, surfaces of the substrates are spaced from each other by the predetermined distance, and the first substrate and the second substrate are joined together in a state where the first substrate and the second substrate are positioned.

6. The method of producing the analytical cell according to claim 5, wherein the solid state joint is formed to seal at least one side of the overlapping portion.

7. The method of producing the analytical cell according to claim 6, further comprising a step of forming a seal by disposing sealant between portions of the first and second substrates at at least one other side of the overlapping portion so that the sealant and the solid state joint together define a liquid-tight space in the overlapping portion in which the electrolytic solution is contained such that the electrolytic solution does not flow.

8. The method of producing the analytical cell according to claim 5, further comprising a step of covering the negative electrode collector and the positive electrode collector with electrically insulating members to prevent side reactions from occurring in the electrode collectors.

* * * * *